(12) United States Patent
Heskestad et al.

(10) Patent No.: US 7,363,813 B2
(45) Date of Patent: Apr. 29, 2008

(54) TEMPERATURE AND MOISTURE PROBE

(75) Inventors: Gunnar Heskestad, Dover, MA (US); Paul A. Croce, Middletown, RI (US)

(73) Assignee: FM Global Technologies, LLC, Johnston, RI (US)

(*) Notice: Subject to any disclaimer, the term of this patent is extended or adjusted under 35 U.S.C. 154(b) by 286 days.

(21) Appl. No.: 10/973,455

(22) Filed: Oct. 27, 2004

(65) Prior Publication Data

US 2006/0086179 A1    Apr. 27, 2006

(51) Int. Cl.
*G01N 19/10* (2006.01)

(52) U.S. Cl. .................. 73/335.06; 73/29.05; 73/77

(58) Field of Classification Search .............. 73/77, 73/335.06, 29.01, 29.02, 29.05
See application file for complete search history.

(56) References Cited

U.S. PATENT DOCUMENTS

| | | | | |
|---|---|---|---|---|
| 2,915,898 A | * | 12/1959 | Van Luik, Jr. | ........... 73/335.05 |
| 3,191,313 A | * | 6/1965 | Moorhouse et al. | .......... 34/561 |
| 3,196,683 A | * | 7/1965 | Gross | ...................... 73/335.08 |
| 3,725,197 A | * | 4/1973 | Dahl et al. | ................... 162/343 |
| 3,886,797 A | | 6/1975 | Bauer | |
| 4,872,340 A | * | 10/1989 | de Yong | ................... 73/335.02 |
| 4,887,466 A | * | 12/1989 | Avery | ...................... 73/335.09 |
| 4,970,969 A | | 11/1990 | Koptis et al. | |
| 4,974,452 A | * | 12/1990 | Hunt et al. | .............. 73/861.64 |
| 5,042,294 A | | 8/1991 | Uzzell | |
| 5,257,532 A | | 11/1993 | Hayakawa et al. | |
| 5,464,044 A | | 11/1995 | Brinkerhoff | |
| 5,520,048 A | * | 5/1996 | Traina et al. | ............ 73/335.06 |
| 6,029,751 A | | 2/2000 | Ford et al. | |
| 6,647,806 B1 | * | 11/2003 | Estrada et al. | ........... 73/861.28 |

* cited by examiner

*Primary Examiner*—Daniel S. Larkin
(74) *Attorney, Agent, or Firm*—Merek, Blackmon & Voorhees, LLC

(57) ABSTRACT

A probe for measuring the temperature and moisture of a gas has an aspirated flow passage with a configuration that causes the gas to have turbulent flow and, therefore, to mix. A dry bulb thermometer and a wet bulb thermometer positioned in the flow passage downstream of the configuration that causes mixing measures the temperature and moisture of the gas. A wick and a water reservoir for keeping the wet bulb thermometer wet are cleaned and refilled by a flow of water through the gas passage. The gas passage is heated to prevent condensation of any moisture in the gas.

20 Claims, 1 Drawing Sheet

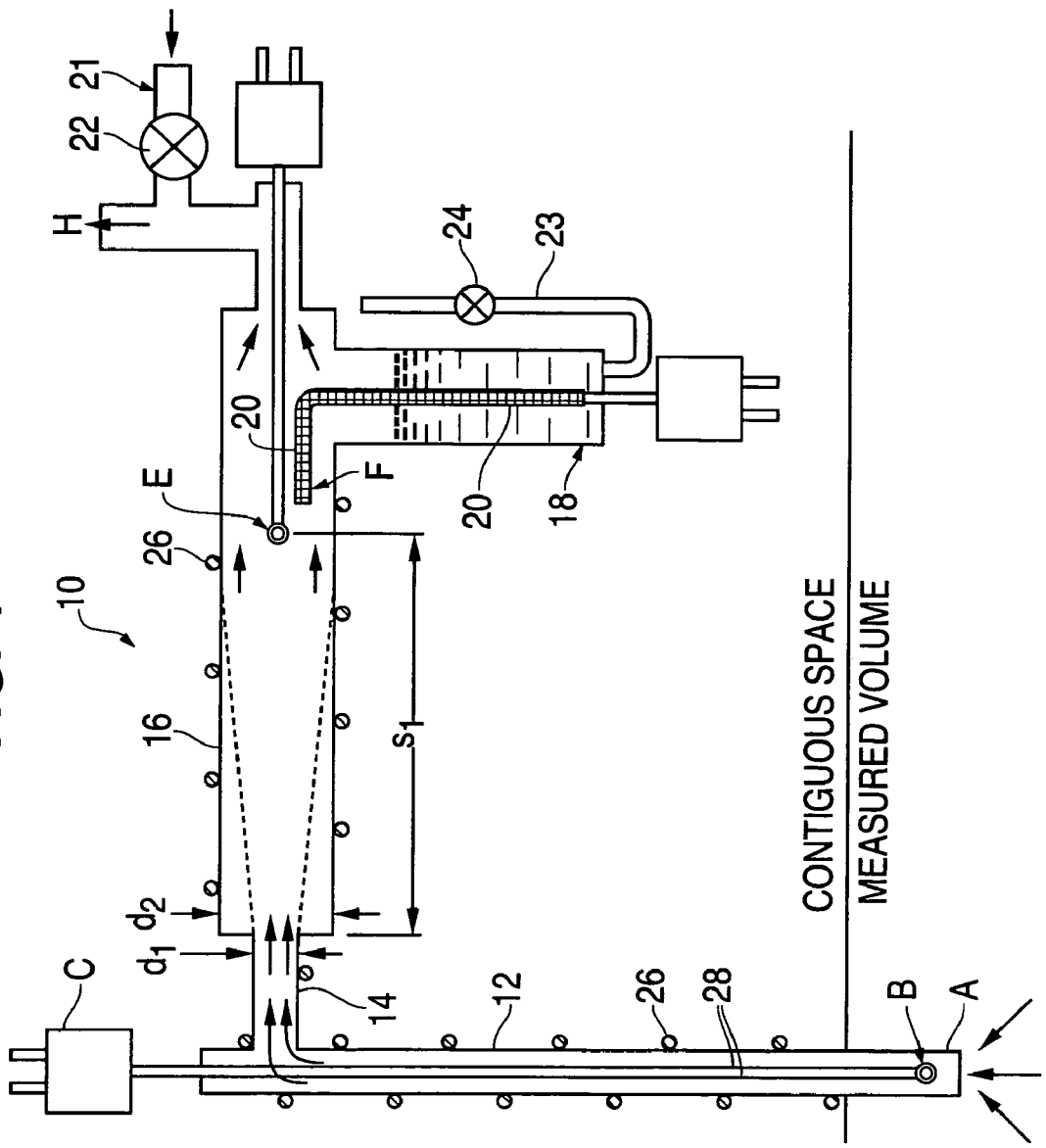

TEMPERATURE AND MOISTURE PROBE

BACKGROUND OF THE INVENTION

The present invention relates to a probe for and a method of measuring the temperature of an aspirated flow together with its moisture content, both in the absence and presence of suspended water droplets in the sampled air volume.

Measurement of temperature in thermally radiating surroundings, as in the presence of fire, is a challenge often met by using radiation shields around a thermocouple (or other thermometer), or by mounting the thermocouple just inside the entrance of an aspirated tube in an arrangement usually referred to as an aspirated thermocouple. A further challenge arises if the measured air or gas also contains suspended water droplets, as in fire tests employing water spray devices such as fire sprinklers. Moreover, the moisture content of the sampled air (mass water vapor per unit mass dry air) may be a required quantity.

SUMMARY OF THE INVENTION

The present invention comprises a combined temperature/moisture aspirated probe and method suitable for use in both a dry and droplet-laden fire environment, or any other environment with heated gas, thermal radiation and suspended water droplets, wherein the probe measures the temperature and moisture content of the gas entering the probe, where the moisture content (mass water vapor per unit mass dry gas) is derived from dry-bulb and wet-bulb determinations in a flow passage, in the aspiration path, that is configured to cause turbulent flow in the gas. Measurements of temperature and moisture can be made in thermally radiating surroundings (such as in a fire) even if the measured gas, such as air, contains suspended water droplets.

BRIEF DESCRIPTION OF THE DRAWING

FIG. 1 is a schematic representation of the temperature/moisture probe.

DETAILED DESCRIPTION OF THE PREFERRED EMBODIMENT

As can be seen from FIG. 1, a probe according to the present invention, which is designated generally by the reference numeral 10, has a gas flow passage, including an inlet A into which an incoming gas, such as air, from a measured volume is aspirated due to an aspirating source at H, such as a source of vacuum. The inlet A is in the measured volume, but most of the probe 10 is in a contiguous space that is separated from the measured volume. An entry thermocouple B is positioned just inside the inlet A to measure the temperature of the incoming gas at that point. The gas flows from the inlet A, through a vertical duct, or tube, 12 and then turns 90 degrees and flows through a horizontal duct, or tube, 14 comprising an upstream portion of the gas flow passage and from the horizontal duct 14 into a further horizontal duct, or tube, 16 of a larger cross-section than the horizontal duct 14, the duct 16 comprising a downstream portion. There is an abrupt change in cross section from the duct 14 to the duct 16, and the change comprises a configuration that causes turbulent flow in the gas. The turbulent flow causes the gas to mix into a uniform state of temperature and velocity. Other configurations that cause uniform temperature and velocity can be used instead.

The duct 12 is vertical, and the ducts 14 and 16 are oriented at an angle to the duct 12 in the illustrated embodiment, because it is convenient for including a water reservoir to be described hereinafter, but other arrangements of the ducts are possible in accordance with the invention. Also in the illustrated embodiment, the horizontal duct 14 has the same cross-sectional size and shape as the vertical duct 12, but it is not required that the horizontal duct 14 have the same cross-sectional size or shape as the vertical duct 12. The horizontal duct 14 has a diameter $d_1$, and the horizontal duct 16 has a diameter $d_2$.

The duct 12 is preferably at least nearly or substantially vertical, and the ducts 14 and 16 are preferably nearly or substantially horizontal, although it is possible that the probe will function in arbitrary orientations. The nearly vertical orientation of the duct 12 prevents ingested water drawn up along the duct wall from possibly dripping onto the bead of the entry thermocouple B, and the nearly horizontal condition of the ducts 14 and 16 prevents water drawn into the larger duct 16 from flowing back into the vertical duct and possibly wetting the bead of the entry thermocouple B.

In the larger horizontal duct 16, the gas flows past a sheathed dry bulb thermocouple E and a sheathed wet bulb thermocouple F, which are close to one another. The thermocouples E and F are positioned downstream of the configuration, that is, the change in the cross sectional area of the flow passage, that causes the gas to mix. Therefore, the gas is mixed by the time it reaches the thermocouples E and F. From the temperature measurements of the thermocouples E and F, the moisture in the gas can be calculated in a known manner.

The probe 10 also has a water reservoir 18 that keeps wet a wick 20 around the wet bulb thermocouple F and, preferably, an arrangement for cleaning the probe and wick and refilling the reservoir. The cleaning and refilling arrangement includes an arrangement 21, including a water source and a valve 22, for selectively feeding water into the probe 10 through the passage that leads to the aspirating source H. The cleaning and refilling arrangement further includes a water level duct, or tube, 23 attached at the bottom of the water reservoir 18. The tube 23 is bent upward, terminating in an open upper end, the elevation of which coincides with the intended initial water level in the reservoir 18. The tube 23 is provided with an on-off valve 24. During back-flushing of the probe 10 and reservoir 18 with water, the valve 24 on the tube 23 is closed, and the backflush exits the probe 10 through the inlet A of the duct 12. In that process, the wick 20, the water reservoir 18, and the interior of the ducts 12, 14 and 16 are all cleaned. Following the backflush, the valve 24 on the tube 23 is opened long enough for the horizontal ducts 14 and 16 to drain into the reservoir 18 and the water level in the reservoir to settle, at which time the valve 24 is closed.

Furthermore, the probe 10 includes a heater 26, for example, an electric resistance heater wire, to electrically heat the probe to the end of the moisture section to prevent condensation of water vapor from the aspirated flow, if condensation would occur otherwise. Condensation would constitute removal of moisture from the gas flow and would lead to inaccurate moisture measurements. It is preferred that heating of the probe 10, when necessary, extend from the lowest portion of the vertical duct 12 that is outside the measured volume to the thermocouples E and F. The region of the larger diameter horizontal duct 16 to the thermocouples E and F is sometimes called the "moisture section".

As can be appreciated from FIG. 1, air is aspirated into the probe at A under the influence of the aspirating source H and flows over the thermocouple B at the end of metal-sheathed thermocouple wires 28 from a thermocouple connector C. Each of the thermocouples E and F also has thermocouple wires and a thermocouple connector. The aspirated air flows up the vertical duct 12 and then turns into the horizontal duct 14, and the horizontal flow expands into the larger diameter horizontal duct 16, where the flow encounters the sheathed dry-bulb thermocouple E and the sheathed wet-bulb thermocouple F, which is kept moist by a wick 20 extending into a water reservoir 18. The flow continues to the aspirating source at H.

An important aspect of the invention is the ratio of the diameters $d_2$ and $d_1$ of the larger and smaller horizontal ducts 16 and 14, respectively, and the ratio of the length $s_1$ of the larger horizontal duct 16, from its inlet to the dry bulb thermocouple E, to the diameter $d_2$ of the larger horizontal duct. The ratio $d_2/d_1$ is the diameter expansion ratio, and the ratio $s_1/d_2$ is the normalized length of the portion of the larger horizontal duct 16 that has the length $s_1$. The proper ratios assure the uniformity of the temperature and velocity of the gas at the positions of the dry and wet bulb thermocouples E and F, respectively. The ratios $d_2/d_1=2$ and $s_1/d_2=5.5$ are near optimum. The portion of the larger horizontal duct 16 having the length $s_1$ is sometimes called the "mixing tube" because, in that portion, there is turbulent mixing which smoothes out radial temperature and velocity variations at the locations of the thermocouples E and F.

The wick 20 of the wet bulb thermocouple F should not touch the sheath of the dry bulb E, and the forward end of the wick is slightly downstream of the dry bulb thermocouple E. The fact that the aspirated flow usually cools down to some extent on the way to the moisture section has no bearing on the moisture content determined from the simultaneous temperatures of thermocouples E and F. If condensation of water vapor from the aspirated flow is known to occur, the probe 10 can be heat traced (heated electrically) to the end of the moisture section.

From experiments on a prototype probe according to the present invention in which the vertical duct 12 had a 5.3 mm inner diameter, it has been deduced that the fire gas temperature measured by the entry thermocouple B of the probe 10 reaches an asymptotically high value in droplet-laden air when the probe flow reaches 15 liters/minute on a room-temperature basis, corresponding to an average air velocity, at room temperature, of 11 meters per second. Compared to the indications of several other thermocouples exposed to the same environment, aspirated and bare, the temperatures indicated by the probe according to the present invention were considerably higher and, hence, from the experience of the inventors, closer to the true gas temperature.

It will be apparent to those skilled in the art and it is contemplated that variations and/or changes in the embodiments illustrated and described herein may be made without departure from the present invention. Accordingly, it is intended that the foregoing description is illustrative only, not limiting, and that the true spirit and scope of the present invention will be determined by the appended claims.

The invention claimed is:

1. A probe for measuring the temperature and moisture of a gas, comprising:
   an aspirated flow passage for the gas, said flow passage having a configuration that causes the gas to have turbulent flow;
   a dry bulb thermometer positioned in the flow passage downstream of said configuration; and
   a wet bulb thermometer positioned in the flow passage downstream of said configuration, whereby the gas is mixed by the time the gas reaches the thermometers.

2. The probe according to claim 1, wherein said flow passage includes an upstream portion having a first flow cross sectional area and a downstream portion having a second flow cross sectional area, wherein said second cross sectional area is larger than said first cross sectional area.

3. The probe according to claim 2, wherein the flow passage increases abruptly from said first cross sectional area to said second cross sectional area.

4. The probe according to claim 2, wherein said flow passage further includes an inlet portion connected to said upstream portion, said inlet portion having an inlet opening for receiving a gas to be measured.

5. The probe according to claim 4, further comprising an entry thermocouple positioned in said inlet portion, near said inlet opening.

6. The probe according to claim 5, wherein said inlet portion is substantially vertical, and said upstream portion is substantially horizontal, whereby any water along the walls of said inlet portion and said upstream portion is prevented from wetting said inlet thermocouple.

7. The probe according to claim 4, further comprising a heater, the heater preventing condensation forming on the probe from any moisture in the gas being measured, wherein said heater heats at least said inlet portion, said upstream portion and said downstream portion from said upstream portion to said wet bulb thermometer.

8. The probe according to claim 7, wherein said heater is an electric resistance heating element contacting said upstream portion and said downstream portion from said upstream portion to said wet bulb thermometer.

9. The probe according to claim 2, wherein said first cross sectional area of said upstream portion has a first diameter, and said second cross sectional area of said downstream portion has a second diameter, wherein the ratio of said second diameter to said first diameter is approximately 2.

10. The probe according to claim 2, wherein said second cross sectional area of said downstream portion has a second diameter, and said downstream portion has a length, wherein the ratio of said length to said second diameter is approximately 5.5.

11. The probe according to claim 1, further comprising a wick and a water reservoir for keeping the wet bulb thermometer wet, and a reservoir cleaning and refilling arrangement.

12. The probe according to claim 11, wherein said reservoir cleaning and refilling arrangement comprises a connection between the water reservoir and a source of water.

13. The probe according to claim 12, wherein said reservoir cleaning and refilling arrangement further comprises a water level duct in fluid communication with the water reservoir and having an open upper end positioned at a desired level of water in the water reservoir.

14. The probe according to claim 13, wherein the water level duct includes a valve selectively permitting water to flow from the water reservoir to the water level duct.

15. The probe according to claim 1, further comprising a heater, the heater preventing condensation forming on the probe from any moisture in the gas being measured.

16. The probe according to claim 1, wherein the dry bulb and wet bulb thermometers comprise thermocouples.

17. A method for measuring the temperature and moisture of a gas, comprising:
   aspirating a flow of the gas through a flow passage having a configuration that causes the gas to have turbulent flow, whereby the gas is mixed;

measuring the temperature of the mixed gas with a dry bulb thermometer downstream of said configuration; and measuring the temperature of the mixed gas with a wet bulb thermometer downstream of said configuration.

18. The method according to claim 17, further comprising measuring the temperature of the gas with a dry bulb thermometer at the inlet of the flow passage.

19. The method according to claim 17, further comprising keeping the wet bulb thermometer wet with a wick and a water reservoir for the wick, and cleaning the reservoir with water flowing through said flow passage when measurements are not being taken.

20. The method according to claim 17, further comprising heating the flow passage in order to prevent condensation from forming on surfaces defining the flow passage from any moisture in the gas.

* * * * *